United States Patent
Schulte et al.

[11] Patent Number: 6,156,024
[45] Date of Patent: *Dec. 5, 2000

[54] ABSORBENT ARTICLES HAVING LOTIONED LEG CUFFS

[75] Inventors: Thomas Edward Schulte, Cincinnati, Ohio; Laura Graves Spalding VanRijswijck, Burlington, Ky.

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/766,386

[22] Filed: Dec. 3, 1996

[51] Int. Cl.$^7$ .............................. A61F 13/15; A61F 13/20
[52] U.S. Cl. ...................... 604/385.28; 604/304; 604/364
[58] Field of Search .............................. 604/385.1, 385.2, 604/359, 360, 364, 365, 381, 375, 304, 385.28, 385.01

[56] References Cited

U.S. PATENT DOCUMENTS

| | | |
|---|---|---|
| 3,489,148 | 1/1970 | Duncan et al. |
| 3,567,820 | 3/1971 | Sperti . |
| 3,585,998 | 6/1971 | Hayford et al. |
| 3,875,942 | 4/1975 | Roberts et al. |
| 3,896,807 | 7/1975 | Buchalter . |
| 4,569,343 | 2/1986 | Kimura et al. |
| 4,623,339 | 11/1986 | Ciraldo et al. ........................ 604/359 |
| 4,666,765 | 5/1987 | Caldwell et al. |
| 4,753,643 | 6/1988 | Kassai ..................... 604/359 |
| 4,790,836 | 12/1988 | Brecher ................... 604/359 |
| 4,959,059 | 9/1990 | Eilender et al. ..................... 604/358 |
| 5,167,653 | 12/1992 | Igaue et al. ........................ 604/385.2 |
| 5,607,760 | 3/1997 | Roe ..................... 442/375 |
| 5,609,587 | 3/1997 | Roe ..................... 604/360 |
| 5,635,191 | 6/1997 | Roe et al. ..................... 604/364 |
| 5,643,588 | 7/1997 | Roe et al. ..................... 604/364 |
| 5,871,763 | 2/1999 | Luu et al. ..................... 424/402 |
| 5,938,649 | 8/1999 | Ducker et al. ..................... 604/363 |

FOREIGN PATENT DOCUMENTS

| | | |
|---|---|---|
| 2019557 | 6/1990 | Canada . |
| 1915452 | 7/1973 | Germany ................ 604/385.1 |
| 4136540 A1 | 5/1992 | Germany . |
| 61-28078 | 2/1986 | Japan . |
| 2-31756 | 2/1990 | Japan . |
| 5-285170 | 11/1993 | Japan . |
| WO 94 09757 | 5/1994 | WIPO . |

*Primary Examiner*—Mark O. Polutta
*Attorney, Agent, or Firm*—Kirsten K. Stone; Caroline Wei-Berk; Bart S. Hersko

[57] ABSTRACT

An absorbent article, such as a diaper, containing leg cuffs coated with a lotion composition is disclosed. The lotions disclosed in the present invention minimize the abrasion between the cuffs and skin in the area where the cuffs contact the wearer's skin, resulting in less skin irritation. The lotion compositions also reduce the adherence of BM to the skin of the wearer, thereby improving the ease of BM clean up. The lotion composition comprises a plastic or fluid emollient such as mineral oil or petrolatum, an immobilizing agent such as a fatty alcohol or paraffin wax to immobilize the emollient on the surface of the diaper leg cuffs, and optionally a hydrophilic surfactant to improve the processability and/or stability of the lotion compositions. Because the emollient is substantially immobilized on the surface of the leg cuff, less lotion is required to impart the desired therapeutic or protective lotion coating benefits.

33 Claims, 4 Drawing Sheets

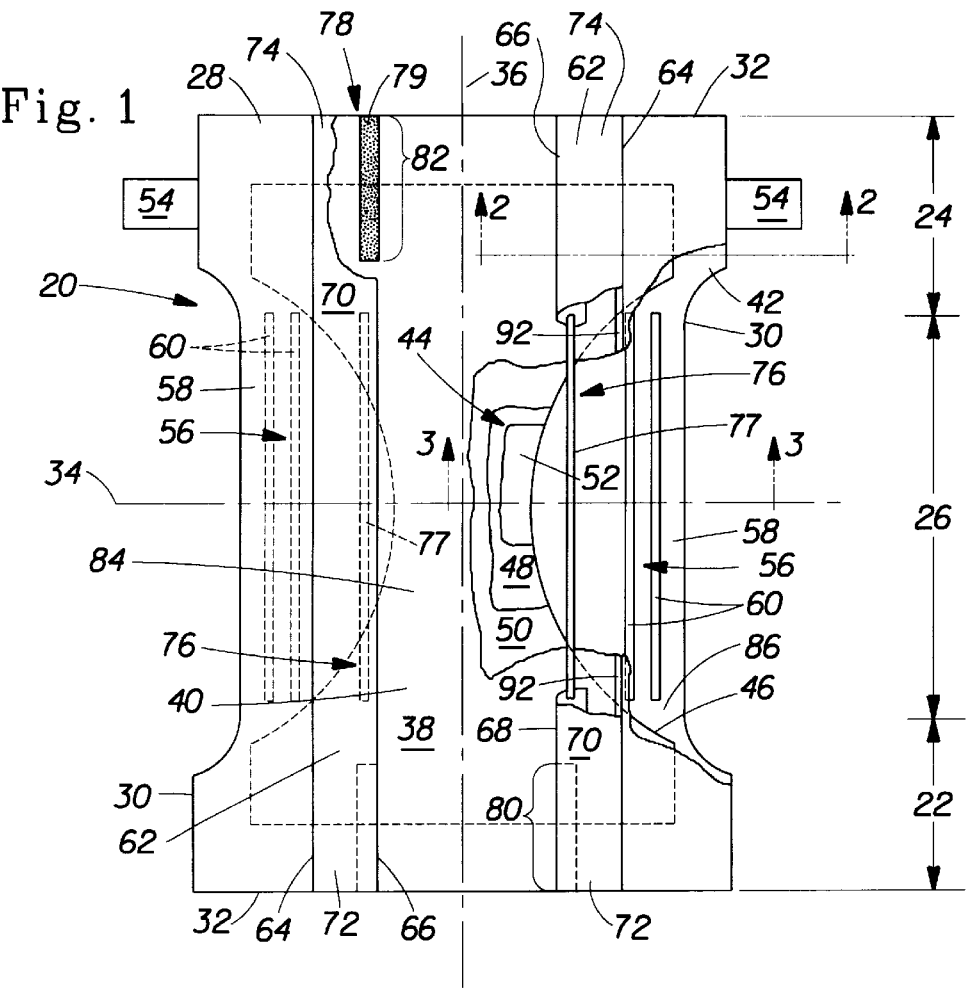
Fig. 1
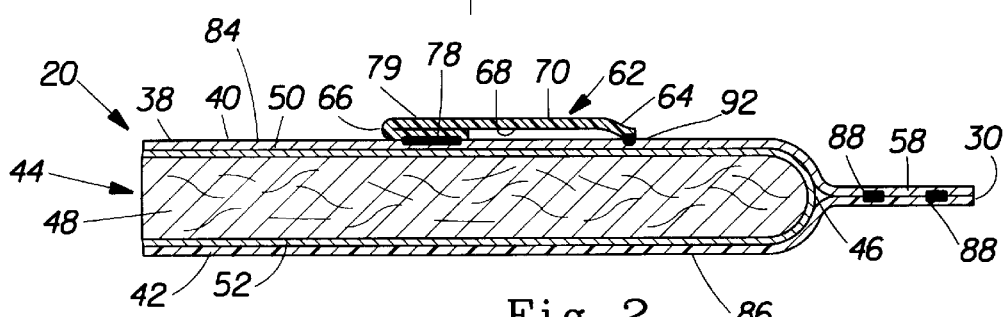
Fig. 2
Fig. 3

ABSORBENT ARTICLES HAVING LOTIONED LEG CUFFS

TECHNICAL FIELD

This application relates to absorbent articles such as diapers, training pants, adult incontinence devices, and the like, having leg cuffs. More particularly, the present invention relates to absorbent articles having a lotion coating on the surface of the leg cuffs that is transferable to the wearer's skin by normal contact and wearer motion and/or body heat. The lotions disclosed in the present invention minimize the abrasion between the cuffs and skin in the area where the cuffs contact the wearer's skin, resulting in less skin irritation.

BACKGROUND OF THE INVENTION

The major function of absorbent articles such as disposable diapers and incontinent briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article and the absorbent article is not able to sustain a good fit on the wearer such that gaps are created allowing the exudates to leak out of the chassis of the absorbent article. For example, urine tends to be deposited into the topsheet in gushes such that the urine migrates to the gaps in the chassis where it can come in contact with clothing or other articles and be absorbed by these articles. Additionally, loose fecal material that is not easily absorbed by the absorbent article tends to "float" on the liquid-receiving surface and work its way past the gaps in the article in the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer to maintain a seal about the leg and minimize gapping. However leakage along the perimeter of the diaper may still occur. As the diaper is worn for longer periods of time, forces tend to act on the diaper to degrade the initial fit on the wearer. Large gaps and sagging of the diaper in the legs and waist are formed by the degradation in fit. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Despite the effectiveness of such structures in containing such material, it has been found that liquids can leak through the barrier cuffs and soil the weareres clothing. In addition, the barrier leg cuffs can cause skin marking in the area where the leg cuff contacts the skin.

It has now been discovered that applying a lotion coating on the surface of the leg cuffs that is transferable to the wearer's skin by normal contact and wearer motion and/or body heat can improve the containment characteristics, reduce skin irritation, of the diaper as well as lead to improved ease of BM clean up. As used herein, the term leg cuff includes barrier leg cuffs, gasket cuffs and combinations and variations thereof. The coating of the cuffs with the lotions disclosed herein can increase the hydrophobicity of the cuffs, thereby improving the leakage performance. The hydrophobic lotion coating allows for flexibility in cuff designs using nonwoven materials by providing an alternate method to achieve the desired hydrophobicity. This can lead to reduced material costs. Importantly, the lotions disclosed in the present invention act to minimize the abrasion between the cuffs and skin in the area where the cuffs contact the wearer's skin, resulting in less skin irritation. The lotions also provide a protective coating on the wearer's skin that helps prevent the adherence of BM to the skin, thereby improving the ease of BM cleanup.

One substance that has been applied as a lotion to diaper products to impart a soothing, protective coating is mineral oil. Mineral oil (also known as liquid petrolatum) is a mixture of various liquid hydrocarbons obtained by distilling the high-boiling (i.e., 300°–390° C.) fractions in petroleum. Mineral oil is liquid at ambient temperatures, e.g. 20°–25° C. As a result, mineral oil is relatively fluid and mobile when applied to diapers. Because mineral oil is fluid and mobile at ambient temperatures, it tends not to remain localized on the body contacting surface of the barrier leg cuffs, but instead migrates through the leg cuffs into the interior of the diaper. Accordingly, relatively high levels of mineral oil need to be applied to the barrier leg cuffs to provide the desired therapeutic or protective coating lotion benefits. This leads not only to increased costs for these lotioned barrier leg cuff diaper products, but other detrimental effects as well, including decreased absorbency of the underlying absorbent core.

Even without increasing its level, the tendency of mineral oil to migrate once applied has other detrimental effects. For example, the applied mineral oil can transfer to, into and through the packaging or wrapper material for the lotioned diaper product. This can create the need for barrier-type packaging or wrapper films to avoid smearing or other leakage of mineral oil from the diaper product.

Accordingly, it would be desirable to provide diaper products having lotioned leg cuffs that: (1) have desirable therapeutic or protective coating lotion benefits (2) do not require relatively high levels of coatings that are liquid at room temperature (e.g., mineral oil) (3) do not adversely affect the absorbency of the diaper product; and (4) do not require special wrapping or barrier materials for packaging.

Therefore, it is an object of the present invention to provide a diaper having lotioned leg cuffs wherein the lotion is transferable to the wearer's skin and provides desirable therapeutic benefits, resulting in less skin irritation.

It is a further object of the present invention to provide a diaper having lotioned leg cuffs wherein the lotion is transferable to the wearer's skin and is effective at reducing the adherence of BM to the skin, thereby improving the ease of BM cleanup.

It is a further object of the present invention to provide a disposable diaper having leg cuffs having improved liquid containment properties.

It is yet a further object of the present invention desirable to provide diapers having lotioned leg cuffs that do not require relatively high levels of mineral oil, and do not require special wrapping or barrier materials for packaging.

These and other objects are obtained using the present invention, as will become readily apparent from a reading of the following disclosure.

SUMMARY OF THE INVENTION

The present invention relates to an absorbent article, such as a disposable diaper, having a lotion coating on the surface of the leg cuffs that is semisolid or solid at ambient temperatures (i.e., at 20° C.) and is adapted to be transferred to the wearer's skin. Upon transfer to the skin, the lotion provides desirable therapeutic and/or protective coating lotion benefits resulting in less skin irritation and also reducing the adherence of BM to the skin of the wearer, thereby improving the ease of BM clean up. The coating of the cuffs with the lotions disclosed herein can also increase the hydrophobicity of the cuffs, thereby improving their leakage performance. The hydrophobic lotion coating allows for flexibility in cuff designs using nonwoven materials by providing an alternate method to achieve the desired hydrophobicity. This can lead to reduced material costs.

Briefly, the absorbent articles of the present invention comprise:

A) a backsheet;
B) a liquid pervious, topsheet joined to said backsheet;
C) an absorbent core positioned between said topsheet and said backsheet; and
D) a barrier leg cuff disposed adjacent each of the absorbent article's two longitudinal side edges, wherein each of said barrier leg cuffs has a proximal edge affixed adjacent to said longitudinal side edge of said absorbent article and a distal edge unsecured to at least a portion of said absorbent article, wherein each of said barrier leg cuffs has an inner surface oriented toward the interior of said absorbent article and an outer surface oriented toward the skin of the wearer when said absorbent article is being worn, wherein at least a portion of said barrier leg cuff outer surface or inner surface has disposed thereon an effective amount of a lotion coating which is semi-solid or solid at 20° C. and which is at least partially transferable to the wearer's skin, said lotion coating comprising:
  (i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, and mixtures thereof; and
  (ii) from about 5 to about 90% of an agent capable of immobilizing said emollient on said outer surface or inner surface of the barrier leg cuff, said immobilizing agent having a melting point of at least about 35° C.

The absorbent article can have two elastically contractible gasketing cuffs in addition to or instead of the barrier leg cuffs. Each elastically contractible gasketing cuff is disposed adjacent each of said two longitudinal side edges of said absorbent article, said gasketing cuffs extending laterally outward from said diaper longitudinal side edges, wherein each of said gasketing cuffs has a front surface oriented toward the skin of the wearer when said diaper is being worn and a back surface opposed to said front surface, wherein at least a portion of said gasketing cuff front surface or back surface has disposed thereon an effective amount of a lotion coating which is semi-solid or solid at 20° C. and which is at least partially transferable to the wearer's skin, said lotion coating comprising:
  (i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, and mixtures thereof; and
  (ii) from about 5 to about 90% of an agent capable of immobilizing said emollient on said front surface or back surface of the gasketing leg cuff, said immobilizing agent having a melting point of at least about 35° C.

The quantity of lotion coating on at least a portion of the body contacting surface of the leg cuffs of the present invention (barrier and/or gasketing cuffs) preferably ranges from about 0.1 mg/in$^2$ to about 50 mg/in$^2$, more preferably from about 1 mg/in$^2$ to about 25 mg/in$^2$. Lotioned leg cuffs according to the present invention provide therapeutic and/or protective lotion coating benefits, as well desirable BM cleaning benefits. In addition, the hydrophobic lotions can improve the cuffs' hydrophobicity and/or provide an alternate means to achieve the desired hydrophobicity. Because the emollient is substantially immobilized on the surface of the leg cuffs, less lotion composition is needed to impart the desired skin care benefits. In addition, special barrier or wrapping materials are preferably not necessary in packaging the lotioned diaper products of the present invention.

As will be discussed hereinafter, the lotion compositions of the present invention preferably have a melting profile such that they are relatively immobile and localized on the diaper leg cuffs at room temperature, are transferable to the wearer at body temperature, and yet are not completely liquid under extreme storage conditions.

Importantly, the lotion compositions of the present invention are easily transferable to the skin by way of normal contact, wearer motion, and/or body heat. Without being bound by theory, it is believed that the lotion composition changes the surface energy of the skin, and/or forms a "barrier" reducing the affinity of the skin for BM or urine. The BM or urine, therefore, has a reduced tendency to stick to the skin, and is easier to remove.

BRIEF DESCRIPTION OF THE DRAWINGS

FIG. 1 is a plan view of a disposable diaper embodiment of the present invention having portions cut away to reveal underlying structure.

FIG. 2 is a fragmentary sectional view taken along section line 2—2 of FIG. 1.

FIG. 3 is a fragmentary sectional view taken along section line 3—3 of FIG. 1.

DETAILED DESCRIPTION OF THE INVENTION

Figure 4:
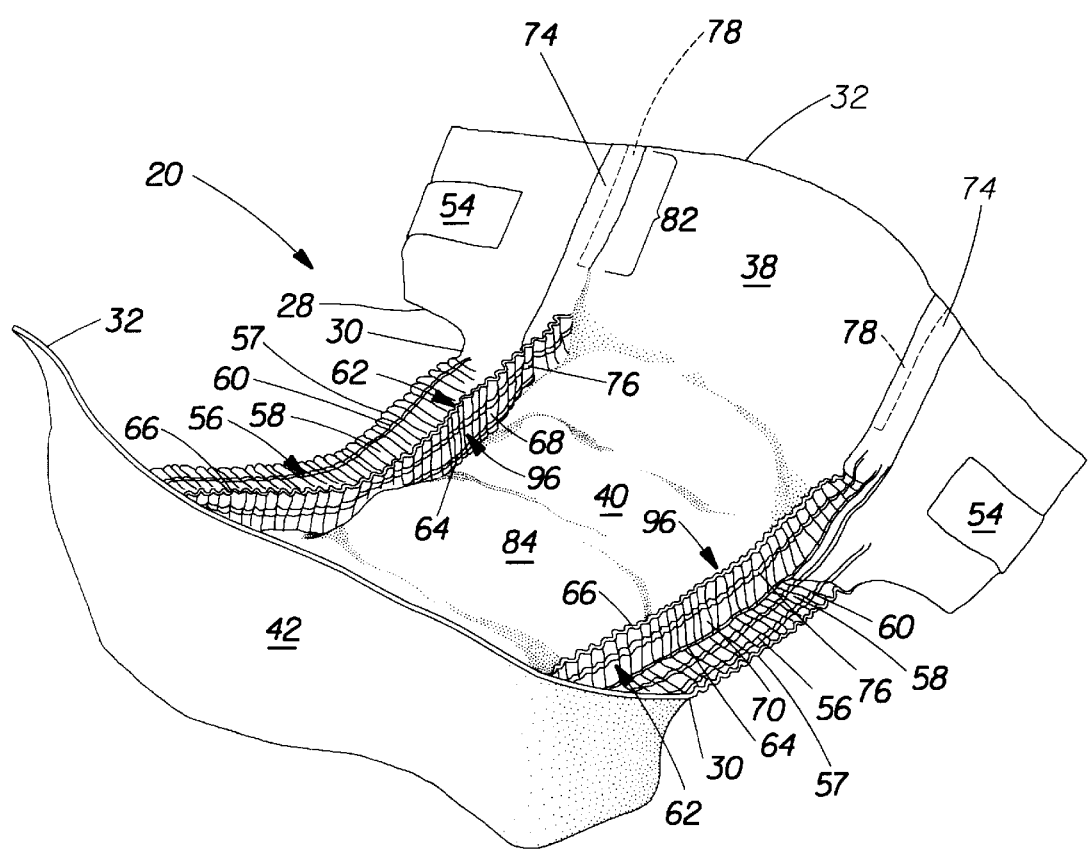
FIG. 4 is a perspective view of an absorbent article in the form of a disposable diaper according to the present invention

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

A. Absorbent Article

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles include feminine hygiene garments such as sanitary napkins and panti-liners, diapers, incontinence briefs, diaper holders, training pants, and the like.

Disposable absorbent articles typically comprise a liquid pervious topsheet, a liquid impervious backsheet joined to the topsheet and an absorbent core positioned between the topsheet and the backsheet. Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side that faces away from the wearer and is oriented toward the wearer's undergarments when the disposable absorbent article is worn.

The following description generally discusses the absorbent core, topsheet, and backsheet materials that are useful in disposable absorbent articles. It is to be understood that this general description applies to these components of the specific absorbent articles shown in FIGS. 1–4 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, symmetric, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is preferably impervious to liquids (e.g., menses and/or urine), at least in the crotch region of the absorbent article, and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment means (not shown in FIG. 3) such as those well known in the art. However, embodiments of the present invention are envisioned wherein portions of the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the lotioned leg cuffs of the present invention may be used are diapers. As used herein, the term "diaper" refers to an absorbent article generally worn by infants, and incontinent persons that is worn about the lower torso of the wearer. In other words, the term "diaper" includes infant diapers, training pants, adult incontinence devices, etc. The present invention is also applicable to other types of disposable products such as sanitary napkins and panty liners that contain leg cuffs.

FIG. 1 is a plan view of a preferred embodiment of the diaper 20 of the present invention in its flat-out, uncontracted state (i.e., with all elastic induced contraction pulled out) with portions of the structure being cut away to more clearly show the construction of the diaper 20 and with the portion of the diaper 20 which contacts the wearer facing the viewer. The diaper 20 is shown in FIG. 1 to have a front waist region 22, a back waist region 24, a crotch region 26 and a periphery 28 which is defined by the outer edges of the diaper in which the longitudinal edges are designated 30 and the end edges are designated 32. The diaper 20 additionally has a lateral centerline which is designated 34 and a longitudinal centerline which is designated 36. The diaper 20 comprises a liquid pervious topsheet 38, the top surface of the topsheet 38 being designated 40; a liquid impervious backsheet 42; an absorbent core 44 having side edges 46 and comprising an absorbent layer 48 and first and second tissue layers 50 and 52, respectively; a pair of tape-tab fasteners 54; gasketing cuffs 56 each comprising a side flap 58 and flap elastic members 60; barrier cuffs 62 each having a proximal edge 64, a distal edge 66, an inner surface 68, an outer surface 70, a first end 72 and a second end 74; and spacing means 76 such as spacing elastic member 77 for spacing the distal edge 66 away from the topsheet top surface 40. The diaper 20 additionally comprises adhesive means 78 such as a glue bead 79 for securing closed the first and second ends 72 and 74 of each barrier cuff 62. The areas in which the adhesive means 78 are disposed are designated front closure zone 80 and back closure zone 82. While the topsheet 38, the absorbent core 44, the backsheet 42, and the elastically contractible gasketing cuffs 56 may be assembled in a variety of well known configurations, a preferred diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

The diaper 20 is shown in FIG. 1 to have an outer surface 86, and an inner surface 84 opposed to the outer surface 86. The inner surface 84 of the diaper 20 comprises that portion of the diaper 20 which is positioned adjacent to the wearers body during use (i.e., the inner surface 84 generally is formed by at least a portion of the topsheet 38 and other components that may be joined to the topsheet 38). The outer surface 86 comprises that portion of the diaper 20 which is positioned away from the wearer's body (i.e., the outer surface 86 generally is formed by at least a portion of the backsheet 42 and other components that may be joined to the backsheet 42). As used herein, the portion of the diaper 20 or component thereof which faces the wearer is also referred to as the body facing surface. Similarly, the portion facing away from the wearer is also referred to herein as the garment facing surface.

FIG. 1 shows a preferred embodiment of the diaper 20 in which the topsheet 38 and the backsheet 42 are coextensive and have length and width dimensions generally larger than those of the absorbent core 44. The topsheet 38 is associated with and superposed on the backsheet 42 to thereby form the periphery 28 of the diaper 20.

The diaper 20 has front and back waist regions 22 and 24 extending, respectively, from the end edges 32 of the diaper periphery 28 toward the lateral centerline 34 of the diaper 20 a distance from about ¼ to about ⅓ the length of the diaper 20. The waist regions comprise those portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

FIG. 2 is a fragmentary sectional view taken along line 2—2 of FIG. 1 and depicts the diaper construction in the back waist region 24 of the diaper 20. (It should be understood that the diaper construction in the front waist region 22 is identical to the construction in the back waist region 24.) The absorbent core comprises the absorbent layer 48 that is shown as being completely enveloped by the first and second tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are adhesively secured together by adhesive 88. In a preferred embodiment, the flap elastic members 60 do not extend into the front waist region 22 so that the gasketing cuff 56 is not formed in this region. The barrier cuff 62 is shown as being a separate element secured to the topsheet 38; the proximal edge 64 being formed by securing the element to the topsheet 38 by adhesive 92. The inner surface 68 of the barrier cuff 62 (also referred to herein as the barrier leg cuff's inboard surface) is secured to the topsheet top surface 40 by adhesive means 78 such as the glue bead 79. Therefore, the distal edge 66 is closed. (i.e., it is not spaced away from the topsheet top surface 40). It should be noted that the spacing elastic member 77 is not disposed in this region because the distal edge 66 is not designed to be spaced away from the topsheet top surface 40 in the waist regions. Therefore, the barrier cuff 62 is not open nor ready to constrain the flow of body exudates in this region.

FIG. 3 is a fragmentary sectional view taken along line 3—3 of FIG. 1 and depicts the diaper construction in the crotch region 26 of the diaper 20 as it is shaped before being applied to the wearer (i.e., the diaper 20 is subjected to elastic contraction). The absorbent core 44 comprises the absorbent layer 48 that is shown as being completely enveloped by the first and second tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are adhesively secured together by adhesive 88. The topsheet 38 and the backsheet 42 also enclose the flap elastic members 60 adjacent the longitudinal edge 30 in the periphery 28. The flap elastic members 60 are secured in the topsheet-backsheet formed side flap 58 by elastic attachment means 90. The elastically contractible gasketing cuff 56 is thereby formed by the side flap 58 and the flap elastic members 60. The gasketing cuff has a front surface 57 orientated toward the skin of the wearer when the diaper is worn, and a back surface 59 opposed to the front surface. The barrier cuff 62 is shown as being formed by securing an element to the topsheet 38 between the flap elastic members 60 and the side edge 46 of the absorbent core 44. The proximal edge 64 of the barrier cuff 62 is formed by securing the barrier cuff element to the topsheet 38 by adhesive 92. The spacing elastic members 77 are enclosed in a tunnel that is formed when an end of the barrier cuff element is folded back upon itself; the spacing elastic members 77 being secured in the barrier cuff 62 by elastic attachments means 94. The distal edge 66 of the barrier cuff is spaced away from the topsheet top surface 40 by the elastic gathering action of the spacing elastic members 77; a channel 96 thereby being formed by at least the proximal edge 64, the distal edge 66 and the inboard surface 68 of the barrier cuff 62. The channel 96 is shown as being ready to restrain, contain and hold body exudates until the diaper 20 is removed from the wearer.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993. Each of these patents is incorporated herein by reference.

A topsheet 38 which is particularly suitable for use in the diaper 20, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 38 of diaper 20 is preferably made of a hydrophilic material to promote rapid transfer of liquids (e.g., urine) through the topsheet. If the topsheet is made of a hydrophobic material, preferably at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of a diaper as described herein, the backsheet 42 has a modified hourglass shape extending beyond the absorbent core a minimum distance of about 1.3 cm to about 6.4 cm (about 0.5 to about 2.5 inch) around the entire diaper periphery.

The absorbent core 44 may take on any size or shape that is compatible with the diaper 20. One preferred embodiment of the diaper 20 has an asymmetric, modified T-shaped absorbent core 44 having ears in the first waist region but a generally rectangular shape in the second waist region. Exemplary absorbent structures for use as the absorbent core of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 20 comprises elasticized barrier leg cuffs 62 and elasticized gasketing cuffs 56 for providing improved containment of liquids and other body exudates; and a fastening system 54 which forms a side closure which maintains the front waist region 22 and the back waist region 24 in an overlapping configuration such that lateral tensions are maintained around the circumference of the diaper to maintain the diaper on the wearer. The diaper 20 may also comprise an elastic waist feature (not shown) and/or elasticized side panels (not shown) in the waist regions 22 and 24 to provide a more comfortable and contouring fit and more effective application of the diaper 20.

The elasticized leg cuffs provide for improved containment of liquids and other body exudates can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003, incorporated herein by reference, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar 20, 1990, and incorporated herein by reference, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, and incorporated herein by reference, describes a disposable diaper having dual cuffs including a gasketing cuff and a barrier cuff. While each elasticized leg cuff may be configured so as to be similar to any of the leg bands, side flaps, barrier cuffs, or elastic cuffs described above, it is preferred that the elasticized leg cuff comprise barrier leg cuffs 62 and gasketing cuffs 56 as described in detail below.

Each barrier cuff 62 is a flexible member having a proximal edge 64, a distal edge 66, an inner surface 68 (also referred to herein as the inboard surface) and an outer surface 70 (also referred to herein as the outboard surface). The inner surface is oriented toward the interior of the diaper, and the outer surface is orientated toward the skin of the wearer when the diaper is being worn. As used herein, the term flexible refers to materials which are compliant and will readily conform to the general shape and contours of the body. The barrier cuff 62 may be manufactured from a wide variety of materials such as polypropylene, polyester, rayon, nylon, foams, plastic films, formed films, and elastic foams. A number of manufacturing techniques may be used to manufacture the barrier cuff. For example, the barrier cuff 62 may be woven, non-woven, spunbonded, spunbonded meltblown spunbounded, carded, coated, laminated or the like. A particularly preferred barrier cuff 62 comprises a polypropylene material containing no finish or surfactant to render it liquid impermeable. A particularly preferred polypropylene material is manufactured by Crown Zellerbach Company as Celestra. In addition, because of the hydrophobic lotion coating of the present invention, the barrier cuff may be made from hydrophilic material As shown in FIGS. 1 and 3, the barrier cuff 62, and more particularly the proximal edge 64, is disposed adjacent to the diaper longitudinal side edge 30, inboard of and preferably adjacent to the gasketing cuff 56. The term "inboard" is defined as the direction toward the centerline (34 or 36, respectively) of the diaper that is parallel to the respective edge of the diaper 20 along which the particular gasketing cuff 56 is disposed. The barrier cuff 62 is disposed inboard of the gasketing cuff 56 so that exudates, especially loose fecal material which is not easily absorbed and tends to float along the topsheet top surface 40, will contact the barrier cuff 62 before it can contact the gasketing cuff 56. The barrier cuff 62 is disposed adjacent the gasketing cuff 56 to provide a more effective dual restraint against the flow of body exudates. The barrier cuff 62 is preferably disposed between the flap elastic member 60 of the gasketing cuff 56 and the longitudinal centerline 36 of the diaper 20. Most preferably, the barrier cuff 62 is disposed between the flap elastic member 60 and the side edge 46 of the absorbent core 44 in the crotch region 26 of the diaper 20.

The proximal edge 64 and the distal edge 66 are in spaced relation to each other and define the width of the barrier cuff 62. The proximal and distal edges 64 and 66, respectively, may be in a parallel, non parallel, rectilinear or curvilinear relationship. In addition, the barrier cuff 62 may have a variety of different cross sectional areas including circular, square, rectangular or any other shape such as shown in FIG. 3. Preferably, the proximal edge 64 is spaced from the distal edge 66 in a parallel and rectilinear relationship to provide a barrier cuff 62 having uniform widths. Each barrier cuff 62 preferably has a width of at least about 5 mm, and preferably from about 10 mm to about 25 mm.

A preferred embodiment of the diaper 20 shown in FIGS. 2 and 3 is provided with the barrier cuff 62 joined to the topsheet 38. The term "joined" includes any means for affixing the barrier cuff 62 to the diaper 20, and includes embodiments wherein the barrier cuff 62 is a separate element having the proximal edge 64 directly or indirectly attached to the topsheet 38 (i.e., integral) or embodiments wherein the barrier cuff 62 is made from the same element or material as the topsheet 38 so that the proximal edge 64 is a continuous and undivided element of the topsheet (i.e., unitary). The barrier cuff 62 may alternatively be joined to the side flap 58, the backsheet 42, the absorbent core 44, the topsheet 38 or any combination of these or other elements of the diaper 20. In a preferred diaper 20, the barrier cuffs 62 are integral with the topsheet 38. The integral barrier cuff 62 is preferably formed by a single strip of material which is secured to the topsheet by adhesive 92, the distal edge 66 being formed by folding an end of the material back upon itself.

The distal edge 66 is preferably disposed inboard of the proximal edge 64 to present a more effective barrier against the flow of exudates. The distal edges 66 are maintained inboard of the proximal edges 64 by the adhesive means 78 so as to obviate their inversion. While the distal edges 66 may alternatively be disposed in other positions in relation to the proximal edges 64, such positions are not preferred.

The distal edge 66 is preferably not secured to any other element in at least the crotch region 26 of the diaper 20 so that it may be spaced away from the top surface 40 of the topsheet 38. The distal edge 66 is preferably spaced away from the top surface 40 of the topsheet 38 so that the barrier cuff 62 may form a channel 96 to enhance the containment of the article. As used herein, "spaced" includes embodiment wherein the distal edges 66 may assume one or more positions relative to the top surface 40 of the topsheet 38 including at some times assuming a position adjacent the top surface 40 of the topsheet 38. The distance between the distal edge 66 to the top surface 40 of the topsheet 38 is measured along a line drawn from the distal edge 66 to the closest part of the topsheet 38 when the distal edge 66 is positioned so as to be spaced away from the topsheet as far as possible. (i.e., in the elastically contracted position). Preferably, the distal edge 66 is spaced away from the topsheet 38 by a height of at least about 2 mm, and more preferably of from about 5 mm (about ¼") to about 10 mm (⅜").

The channel 96 is formed at least along the proximal and distal edges 64 and 66 and the inboard surface 68 of the barrier cuff 62. The channel 96 forms a barrier to the flow of exudates as they tend to move or float across the topsheet 38. Thus the channel 96 holds and contains exudates until the diaper 20 can be removed.

In addition to barrier leg cuffs, the absorbent articles of the present invention preferably comprise gasket cuffs 56. The elastically contractible gasketing cuffs 56 are disposed adjacent the periphery 28 of the diaper 20, preferably along each longitudinal edge 30 so that the gasketing cuffs 56 tend to draw and hold the diaper 20 against the legs of the wearer. While the gasketing cuffs 56 may comprise any of several means as are well known in the diaper art, a particularly preferred gasketing cuff construction comprises a flexible side flap 58 and a flap elastic member 60, as is described in detail U.S. Pat. No. 3,860,003, issued to Buell on Jan. 14, 1975 and incorporated herein by reference. In addition, a method and apparatus suitable for manufacturing a disposable diaper having elastically contractible gasketing cuffs 56 are described in U.S. Pat. No. 4,081,301 entitled "Method and Apparatus for Continuously Attaching Discrete, Stretched Elastic Strands to Predetermined Isolated Portions of Disposable Absorbent Articles" which issued to K. B. Buell on Mar. 28, 1978 and which patent is incorporated herein by reference.

The side flap 58 should be highly flexible and thus contractible so that the flap elastic members 60 may gather the side flap 58 to provide a gasketing cuff 56 about the legs or waist of the wearer. The side flaps 58 are that portion of the diaper 20 between the periphery 28 and the edges of the absorbent core 44. Thus in a preferred embodiment of the present invention as shown in FIG. 1, the side flaps 58 are formed from the extension of the backsheet 42 and the topsheet 38 from and along the side edges 46 of the absorbent core 44 of the diaper 20 in at least the crotch region 26.

The flap elastic members 60 are secured to the side flaps 58 in an elastically contractible condition so that in a normally unrestrained configuration, the flap elastic members 60 effectively contract or gather the side flaps 58. The flap elastic members 60 can be secured to the side flaps 58 in an elastically contractible condition in at least two ways. For example, the flap elastic members 60 may be stretched and secured to the side flaps 58 while the side flaps 58 are in an uncontracted condition. Alternatively, the side flaps 58 may be contracted, for example by pleating, and the flap elastic members 60 secured to the contracted side flaps 58 while the flap elastic members 60 are in their unrelaxed or unstretched condition.

In the embodiment illustrated in FIG. 1, the flap elastic members 60 extend essentially the entire length of the side flaps 58 in the crotch region 26 of the diaper 20. Alternatively, the elastic members 60 may extend the entire length of diaper 20, or any other length suitable to provide an elastically contractible gasketing cuff. The length of the flap elastic members 60 is dictated by the diaper's design.

In the diaper 20 of FIG. 3, the flap elastic members 60 are associated with the side flaps 58 by securing them to the side flaps 58 with elastic attachments means 90. The elastic attachment means 90 should be flexible and of sufficient adhesiveness to hold the flap elastic member in its stretched condition. The elastic attachment means 90 herein are preferably glue beads made of hot melt adhesives such as marketed by Findley Adhesives Incorporated, Elm Grove, Wis. as Findley Adhesives 581. A more detailed description of the manner in which the flap elastic members 60 may be positioned and secured to the diaper 20 can be found in U.S. Pat. No. 4,253,461 issued to Strickland and Visscher on Mar. 3, 1981, and U.S. Pat. No. 4,081,301 issued to Buell on Mar. 28, 1978, both of which are incorporated herein by reference.

One flap elastic member 60 which has been found to be suitable is an elastic strand having a cross section of 0.18 mm by 1.5 mm and made from natural rubber as available from Easthampton Rubber Thread Company of Stewart, Va., under the trademark L-1900 Rubber Compound. Other suitable flap elastic members 60 can be made from natural rubber, such as elastic tape sold under the trademark Fulflex 9211 by Fulflex Company of Scotland, N.C. The flap elastic member 60 may also comprise any heat shrinkable elastic material as is well known in the art. Other suitable flap elastic members 60 may comprise a wide variety of materials as are well known in the art including elastomeric films, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear. Still further, the flap elastic members 60 may be affixed to the diaper 20 in any of several ways which are well known in the art. For example, the flap elastic members 60 may be ultrasonically bonded, heat/pressure sealed into the diaper 20 using a variety of bonding patterns or the elastic members 60 may simply be glued to the diaper 20.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 54 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B14,662,875, issued to Hirotsu et al. on May 5, 1987; and U.S. Pat. No. 5,151,092, issued to Buell et al. on Sep. 29, 1992; each of which is incorporated herein by reference.

FIG. 4 is a perspective view of the diaper 20 in its elastically contracted position prior to being placed on the wearer. The topsheet 38 is shown as the body contacting surface of the diaper 20, the backsheet 42 being disposed away from the body of the wearer. The gasketing cuffs 56 are shown to be gathered or contracted by the flap elastic members (not shown in FIG. 4). The diaper 20 is shown as having two barrier cuffs 62 extending adjacent to and inboard of the gasketing cuffs 56. The distal edges 66 are shown to be gathered and contracted by the spacing elastic members (not shown) in the crotch region 26 so as to provide a longitudinally extending channel 96 along the diaper 20. In addition, the ends 72 and 74 of the barrier cuff 62 are secured closed in the front and back closure zones 80 and 82, respectively, so as to provide comfort for the wearer, to obviate inversion of the barrier cuffs, and for ease of application of the diaper.

The diaper 20 is applied to a wearer, by positioning the back waist region 24 under the wearer's back, and drawing the remainder of the diaper 20 between the wearer's leg so that the front waist region 22 is positioned across the front of the person. The ends of the tape-tab fasteners 54 are then secured preferably to outwardly facing areas of the diaper 20. In this manner, the barrier cuffs 62 should be disposed in the crotch region of the wearer and should provide the dispositions and functions described hereinbefore. Once applied, the distal edges 66 of the barrier cuffs 62 extend through the groin areas and diverge upwardly along both of the buttocks of the wearer. Neither of the barrier cuffs 62 encircle the thighs of the wearer. However, the gasketing cuffs 56 will encircle the thighs and create a gasketing action against the thighs. The ends of the barrier cuff 62 are secured to the topsheet 38 to obviate the inversion of the barrier cuffs, for comfort for the wearer during application and use, and for ease of application.

The lotioned cuffs of the present invention are also useful in training pants. The term "training pants", as used herein, refers to disposable garments having fixed sides and leg openings. Training pants are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993. The lotioned cuffs of the present invention are also applicable to absorbent articles that are a combination or "hybrid" of training pants and diapers.

Another disposable absorbent article for which the lotioned topsheets of the present invention are useful are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 071637,090 filed by Noel, et al. on Jan. 3, 1991 (PCT Publication No. WO 92/11830 published on Jul. 23, 1992).

B. Lotion Composition

The lotion compositions of the present invention are solid, or more often semisolid, at 20° C., i.e. at ambient temperatures. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components.

The lotion compositions of the present invention are at least semi-solid at room temperature to minimize lotion migration. In addition, the lotion compositions preferably have a final melting point (100% liquid) above potential "stressful" storage conditions that can be greater than 45° C. (e.g., warehouse in Arizona, car trunk in Florida, etc.). Specifically, the lotion compositions of the present invention should have the following melt profile:

| Characteristic | Preferred Range | Most Preferred |
|---|---|---|
| % liquid at room temp. (20° C.) | 2–50 | 3–25 |
| % liquid at body temp. (37° C.) | 25–95 | 30–90 |
| final melting point (° C.) | $\geq 38$ | $\geq 45$ |

By being solid or semisolid at ambient temperatures, these lotion compositions do not have a tendency to flow and migrate into the interior of the diaper to which they are applied. This means less lotion composition is required for imparting desirable therapeutic or protective coating lotion benefits.

As used herein, the term "leg cuff" is inclusive of both barrier cuffs 62, gasketing cuffs 56, and combinations and variations thereof.

In preparing lotioned diaper products according to the present invention, the lotion composition is preferably applied to the body contacting surface (i.e., body facing surface) of a diaper leg cuff. As defined herein, the body contacting surface of a barrier leg cuff is normally the outer surface, and the body contacting surface of a gasketing leg cuff is normally the front surface. However, lotion can penetrate through some of the cuff materials, so applying lotion to the garment contacting surface of the leg cuffs (i.e, barrier leg cuff inner surface and/or gasketing leg cuff back surface) is also expressly within the scope of the present invention.

When applied to the above-described surfaces of the leg cuffs, the lotion compositions of the present invention are transferable to the wearer's skin by normal contact, wearer motion, and/or body heat. Importantly, the lotions disclosed in the present invention minimize the abrasion between the cuffs and skin in the area where the cuffs contact the wearer's skin, resulting in less skin irritation.

The diaper barrier leg cuffs of the present invention and/or the gasketing leg cuffs contain an effective amount of the lotion composition. As used herein, the term "effective amount of a lotion coating" refers to an amount of a particular lotion composition which, when applied to a diaper leg cuff will be effective in reducing the abrasion between the cuffs and skin in the area where the cuffs contact the wearer's skin, resulting in less skin irritation. The lotions are also effective in reducing the adherence of BM to the skin of the wearer. Of course, the effective amount of a lotion coating will depend, to a large extent, on the particular lotion composition used.

The lotion compositions of the present invention comprise: (1) an emollient(s); (2) an immobilizing agent(s) for the emollient; (3) optionally a hydrophilic surfactant(s); and (4) other optional components.

The viscosity of the formulated lotion compositions, including emollient, immobilizing agent, and optional components should be as high as possible to keep the lotion from flowing into the interior of the diaper. Unfortunately, high viscosities can also lead to lotion compositions that are difficult to apply without processing problems. Therefore, a balance must be achieved so the viscosities are high enough to keep the lotion compositions localized on the body contacting surface of the diaper leg cuffs, but not so high as to cause processing problems. Suitable viscosities for the lotion compositions will typically range from about 1 to about 5000 centipoises, preferably from about 5 to about 200 centipoises, more preferably from about 10 to about 100 centipoises measured at 60° C.

1. Emollient

The key active ingredient in these lotion compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. For the purposes of the present invention, these emollients have either a plastic or fluid consistency at 20° C., i.e., at ambient temperatures. This particular emollient consistency allows the lotion composition to impart a soft, lubricious, lotion-like feel.

The emollients useful in the present invention are also substantially free of water. By "substantially free of water" is meant that water is not intentionally added to the emollient. Addition of water to the emollient is not necessary in preparing or using the lotion compositions of the present invention and could require an additional drying step. However, minor or trace quantities of water in the emollient that are picked up as a result of, for example, ambient humidity can be tolerated without adverse effect. Typically, the emollients used in the present invention contain about 5% or less water, preferably about 1% or less water, most preferably about 0.5% or less water.

Emollients useful in the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum" and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for lotion compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use in the present invention include polysiloxane compounds. In general suitable polysiloxane materials for use in the present invention include those having monomeric siloxane units of the following structure:

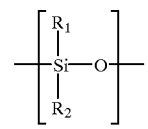

(1)

wherein, $R_1$ and $R_2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit. Additionally, the polysiloxane can be either a straight chain, a branched chain or have a cyclic structure. The radicals $R_1$ and $R_2$ can additionally independently be other silaceous functionalities such as, but not limited to siloxanes, polysiloxanes, silanes, and polysilanes. The radicals $R_1$ and $R_2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the diaper leg cuffs. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the diaper leg cuffs by such methods as, for example, emulsifying the polysiloxane in surfactant or providing the polysiloxane in solution with the aid of a solvent, such as hexane, listed for exemplary purposes only. Particular methods for applying polysiloxane emollients to diaper leg cuffs are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the lotion compositions of the present invention include phenyl-functional polymethylsiloxane compounds (e.g., Dow Corning 556 Cosmetic-Grade Fluid: polyphenylmethylsiloxane), dimethicone compounds, and cetyl or stearyl functionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petroleum-based emollients, fatty acid ester emollients, fatty acid ester ethoxylates, alkyl ethoxylate emollients fatty alcohol emollients, and polysiloxanes, the emollients useful in the present invention can include minor amounts (e.g., up to about 10% of the total emollient) of other, conventional emollients. These other conventional emollients include, but are not limited to propylene glycol, glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$–$C_{28}$ fatty acids; other fatty esters of polyhydroxy alcohols; lanolin and its derivatives, and cod liver oil. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 10 to about 95% of the emollient. Preferably, the lotion composition comprises from about 20 to about 80%, most preferably from about 40 to about 75%, of the emollient.

2. Immobilizing Agent

An especially key component of the lotion compositions of the present invention is an agent capable of immobilizing the emollient on the diaper leg cuff to which the lotion composition is applied. Because the emollient in the composition has a plastic or fluid consistency at 20° C., it tends to flow or migrate, even when subjected to modest shear. When applied to a diaper leg cuff, especially in a melted or molten state, the emollient will not remain primarily on the surface of the leg cuff. Instead, the emollient will tend to migrate and flow into the interior of the diaper.

This migration of the emollient into the interior of the diaper can cause undesired effects on the absorbency of the diaper core due to the hydrophobic characteristics of many of the emollients used in the lotion compositions of the present invention. Also, migration of lotion through the cuff can cause can have an adverse effect on the sustained elasticity of the elastic gathers. It also means that much more emollient has to be applied to the diaper leg cuff to get the desired therapeutic or protective lotion benefits. Increasing the level of emollient not only increases the cost, but also exacerbates the undesirable effect on the absorbency of the diaper core, as well on the performance of the contracted or elastic gathers.

The immobilizing agent counteracts this tendency of the emollient to migrate or flow by keeping the emollient primarily localized on the surface of the diaper leg cuff to which the lotion composition is applied. This is believed to be due, in part, to the fact that the immobilizing agent raises the melting point of the lotion composition above that of the emollient. Since the immobilizing agent is also miscible with the emollient (or solubilized in the emollient with the aid of an appropriate emulsifier), it entraps the emollient on the surface of the diaper leg cuff as well.

It is also advantageous to "lock" the immobilizing agent on the surface of the diaper leg cuff. This can be accomplished by using immobilizing agents which quickly crystallize (i.e., solidify) at the surface of the leg cuff. In addition, outside cooling of the treated diaper leg cuff via blowers, fans, etc. can speed up crystallization of the immobilizing agent.

In addition to being miscible with (or solubilized in) the emollient, the immobilizing agent needs to have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

Suitable immobilizing agents for the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear.

Importantly, these preferred immobilizing agents such as the $C_{16}$–$C_{18}$ fatty alcohols increase the rate of crystallization of the lotion causing the lotion to crystallize rapidly onto the surface of the substrate. Lower lotion levels can therefore be utilized or a superior lotion feel can be delivered. Traditionally, greater amounts of lotion were needed to generate softness because of the flow of these liquids into the diaper core.

Other types of immobilizing agents can be used either alone or in combination with the fatty alcohols, fatty acids, and fatty alcohol ethoxylates described above. Examples of these other types of immobilizing agents includes polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using diaper leg cuffs to which the lotion composition is applied, these esters and amides should also be relatively mild and non-irritating to the skin.

Suitable polyhydroxy fatty acid esters for use in the present invention will have the formula:

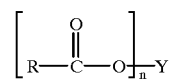

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose;

sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di- stearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174, 927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly –$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxpropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

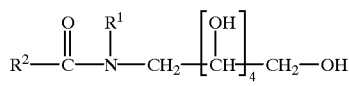

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, beeswax, candelilla, paraffin, ceresin, esparto, ouricuri, rezowax, and other known waxes. Preferably the wax is a paraffin wax. An example of a particularly preferred paraffin wax is Parrafin S. P. 434 from Strahl and Pitsch Inc. P.O. Box 1098 West Babylon, N.Y. 11704.

The amount of immobilizing agent that should be included in the lotion compositions will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 90% of the immobilizing agent. Preferably, the lotion composition comprises from about 5 to about 50%, most preferably from about 10 to about 40%, of the immobilizing agent.

3. Optional Hydrophilic Surfactant

Depending upon the particular immobilizing agent used in the lotion composition of the present invention, an additional hydrophilic surfactant (or a mixture of hydrophilic surfactants) may optionally be used to improve processability and/or stability of the lotions.

Suitable hydrophilic surfactants will be miscible with the emollient and the immobilizing agent so as to form homogeneous mixtures. Because of possible skin sensitivity of those using disposable absorbent products to which the lotion composition is applied, these surfactants should also be relatively mild and non-irritating to the skin. Typically, these hydrophilic surfactants are nonionic to be not only non-irritating to the skin, but also to avoid other undesirable effects on any underlying tissue laminate structure, e.g., reductions in tensile strength.

Suitable nonionic surfactants may be substantially non-migratory after the lotion composition is applied to the diaper leg cuffs and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in lotion compositions of the present invention include alkylglycosides; alkylglycoside ethers as described in U.S. Pat. No. 4,011,389 (Langdon, et al), issued Mar. 8, 1977; alkylpolyethoxylated esters such as Pegosperse IGOOMS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to improve the processability and/or stability of the lotion composition will depend upon the type of emollient and immobilizing agent used, the HLB value of the surfactant used and like factors. The lotion compositions of the present invention can optionally comprise from about 1 to about 50% of the hydrophilic surfactant, more preferably from about 1 to about 25%, by weight of the hydrophilic surfactant.

4. Other Optional Components

Lotion compositions can comprise other optional components typically present in emollient, creams, and lotions of this type. These optional components include water, viscosity modifiers, perfumes, disinfectant antibacterial actives, pharmaceutical actives, film formers, vitamins (e.g., vitamin E), deodorants, opacifiers, astringents, solvents and the like. Materials such as zinc oxide, calamine, and allantoin can also be used to help protect the skin from irritation and diaper rash. In addition, stabilizers can be added to enhance the shelf life of the lotion composition such as cellulose derivatives, proteins and lecithin. All of these materials are well known in the art as additives for such formulations and can be employed in appropriate amounts in the lotion compositions of the present invention. In addition, aloe extract in amounts from about 0.1% to about 20% by weight is a preferred optional component for the lotion components disclosed herein.

C. Treating Diaper Leg Cuffs With Lotion Composition

In preparing lotioned diaper products according to the present invention, the lotion composition is preferably applied to the body contacting surface (i.e., body facing surface) of a diaper leg cuff. As defined herein, the body contacting surface of a barrier leg cuff is normally the outer surface and the body contacting surface of a gasketing leg cuff is normally the front surface. However, lotion can penetrate through some of the cuff materials, so applying lotion to the garment contacting surface of the leg cuffs (i.e, barrier leg cuff inner surface and/or gasketing leg cuff back surface) is also expressly within the scope of the present invention.

Any of a variety of application methods that evenly distribute lubricious materials having a molten or liquid consistency can be used. Suitable methods include spraying, printing (e.g., flexographic printing), coating (e.g., gravure or slot coating), extrusion, or combinations of these application techniques, e.g. spraying the lotion composition on a rotating surface, such as a calender roll, that then transfers the composition to the body contacting surface of the diaper leg cuffs. If desired, lotion can also be applied to both sides of the cuffs to improve the cuffs hydrophobicity.

The manner of applying the lotion composition to the diaper leg cuffs should be such that the leg cuffs do not become saturated with the lotion composition. If the leg cuffs becomes saturated with the lotion composition, there is a greater potential for the loton to migrate into the interior of the diaper where it can have a deterimental effect on the absorbency of the underlying absorbent core. Also, saturation of the leg cuffs is not required to obtain the therapeutic and/or protective lotion benefits. Particularly suitable application methods will apply the lotion composition primarily to the body contacting surface of the diaper leg cuff. However, lotion can penetrate through some of the cuff materials, so applying lotion to the garment contacting surface of the leg cuffs is also within the scope of the present invention.

The minimum level of lotion to be applied to the diaper leg cuff is the smallest amount effective in reducing the abrasion between the cuffs and skin in the area where the cuffs contact the weareres skin, thereby resulting in less skin irritation. The lotions are also effective in reducing the adherence of BM to the skin of the wearer. Of course, the effective amount of a lotion coating will depend, to a large extent, on the particular lotion composition used. The lotion composition is preferably applied to the diaper leg cuffs of the present invention in an amount ranging from about 0.1 mg/in$^2$ to about 50 mg/in$^2$ more preferably from about 1 mg/in$^2$ to about 25 mg/in$^2$ (mg of lotion per square inch of coated leg cuff. Because the emollient is substantially immobilized on the surface of the leg cuff, less lotion composition is needed to impart the desired skin care benefits. Such relatively low levels of lotion composition are adequate to impart the desired therapeutic and/or protective lotion benefits to the leg cuff.

The lotion composition may be applied evenly and uniformly onto either or both surfaces of the leg cuff or portions thereof. The lotion coating may also be patterned (i.e., stripes, boxes, dots, spirals, etc.) Preferably, the lotion composition is registered with the region of the leg cuff that will, in use, be most in contact with the wearer and is applied in a stripe aligned with and centered on the longitudinal centerline of each cuff. Most preferably, as described in the Examples hereinafter, the lotion composition is applied in a stripe to a discrete portion of the barrier leg cuff , e.g., a 1.4 inch wide (diaper lateral direction) and 11.75 inch long (diaper longitudinal direction) patch generally disposed in the crotch portion of the inner surface of the barrier leg cuff.

The lotion composition can also be applied nonuniformly to either or both surfaces of the diaper leg cuff. By "nonuniform" is meant that the amount, pattern of distribution, etc. of the lotion composition can vary over the leg cuff surface. For example, some portions of the treated surface of the leg cuff can have greater or lesser amounts of lotion composition, including portions of the surface that do not have any lotion composition on it.

The lotion composition can be applied to the leg cuff at any point during assembly. For example, the lotion composition can be applied to the leg cuff of the finished disposable absorbent product before it has been packaged. The lotion composition can also be applied to the leg cuff before it is combined with the other raw materials to form a finished disposable absorbent product.

The lotion composition is typically applied from a melt thereof to the diaper leg cuff. Since the lotion composition melts at significantly above ambient temperatures, it is usually applied as a heated coating to the leg cuff. Typically, the lotion composition is heated to a temperature in the range from about 35° to about 100° C., preferably from 40° to about 90° C., prior to being applied to the diaper leg cuff. Once the melted lotion composition has been applied to the diaper leg cuff, it is allowed to cool and solidify to form solidified coating or film on the surface of the leg cuff. Preferably, the application process is designed to aid in the cooling/set up of the lotion.

Figure 5:
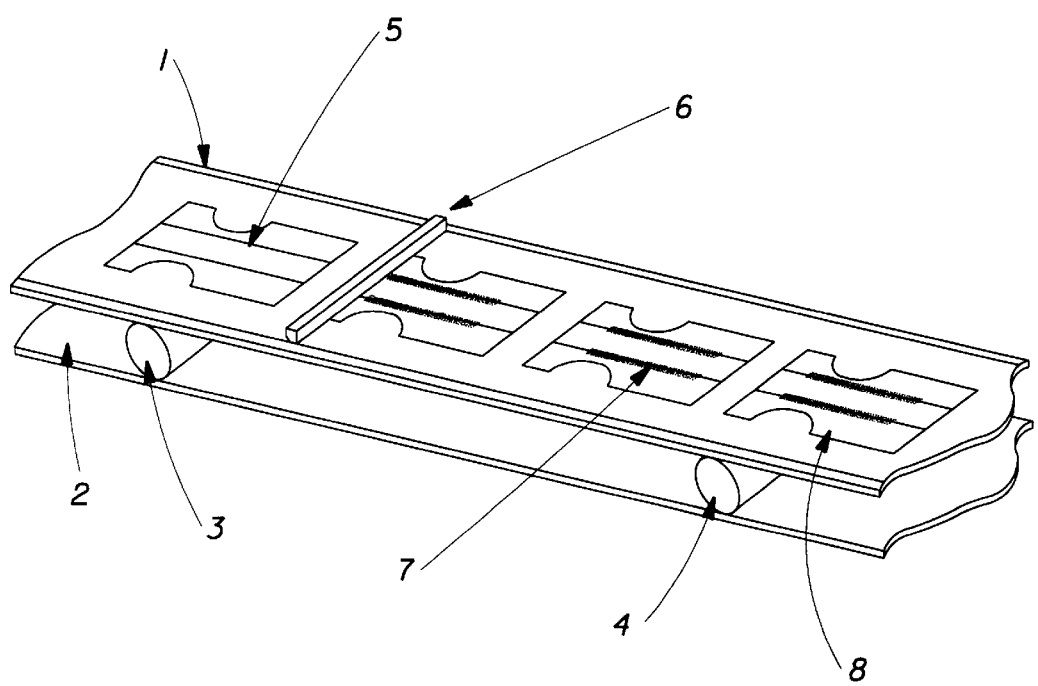
FIG. 5 is a schematic representation illustrating a preferred process for applying the lotion composition of the present invention to diaper barrier leg cuffs.

In applying lotion compositions of the present invention to diaper leg cuffs, slot coating, extrusion coating, gravure coating, and spraying methods are preferred. FIG. 5 illustrates a preferred method involving continuous or intermittent contact slot coating of the lotion composition on to a diaper barrier leg cuff during the converting operation. Referring to FIG. 5, conveyor belt 1 advances in the direction shown by the arrows on turning rolls 3 and 4 and becomes returning conveyor belt 2. Conveyor belt 1 carries nonlotioned diaper 5 to contact slot coating station 6 where barrier leg cuff patch 7 is coated with a hot, molten (e.g., 65° C.) lotion composition. After leaving slot coating station 6, nonlotioned diaper 5 becomes lotioned diaper 8 having lotioned barrier leg cuffs. The amount of lotion composition transferred to barrier leg cuff patch 7 is controlled by: (1) the rate at which the molten lotion composition is applied from contact slot coating station 6; and/or (2) the speed at which conveyor belt 1 travels under slot coating station 6.

Figure 6:
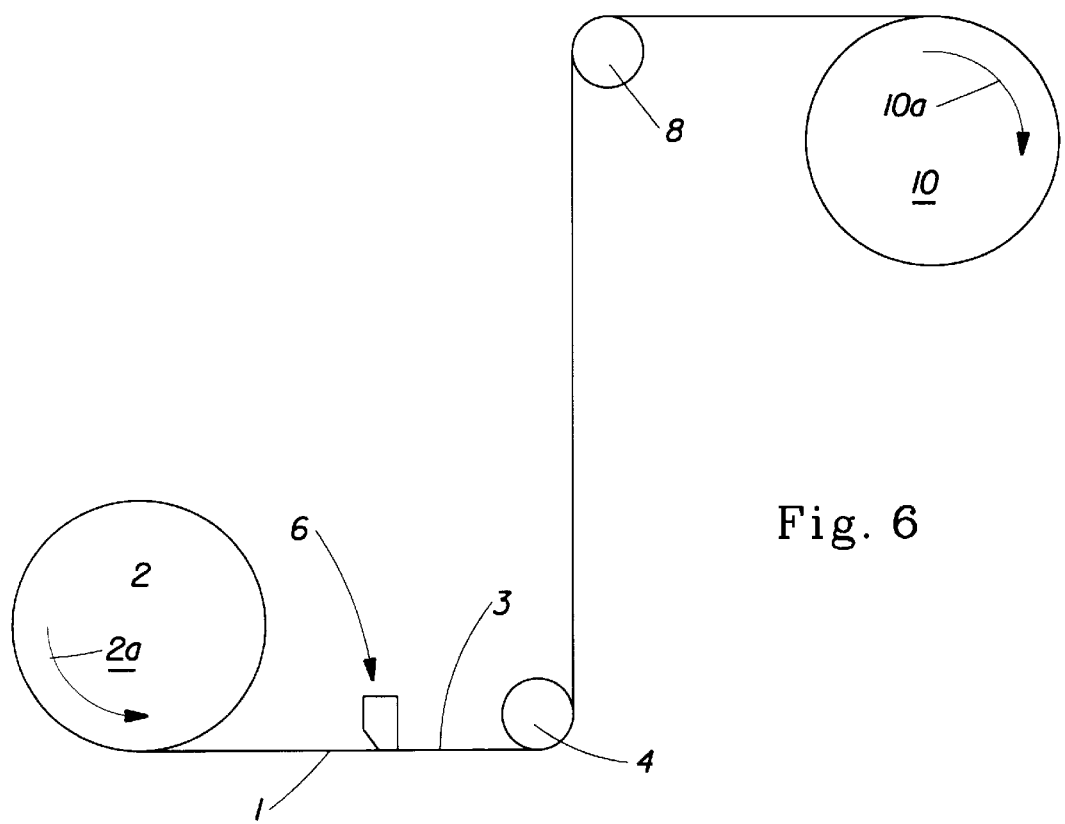
FIG. 6 is a schematic representation illustrating an alternative process for applying the lotion composition of the present invention to diaper barrier leg cuffs.

FIG. 6 illustrates an alternate preferred method involving contact slot coating of the lotion composition on the diaper barrier leg cuffs before the leg cuffs are assembled with the other raw materials into a finished product. Referring to FIG. 6, a nonwoven barrier leg cuff web 1 is unwound from parent barrier leg cuff roll 2 (rotating in the direction indicated by arrow 2a) and advanced to the contact slot coating station 6 where one side of the web is coated with a hot, molten (e.g., 65° C.) lotion composition. After leaving slot coating station 6, nonwoven barrier leg cuff web 1 becomes a lotioned barrier leg cuff web indicated by 3. Lotioned barrier leg cuff web 3 is then advanced around turning roll 4 and turning roll 8, and then wound up on lotioned barrier leg cuff parent roll 10 (rotating in the direction indicated by arrow 10a).

SPECIFIC ILLUSTRATIONS OF THE PREPARATION OF LOTIONED DIAPER BARRIER LEG CUFFS ACCORDING TO THE PRESENT INVENTION

The following are specific illustrations of treating diaper barrier leg cuffs with lotion compositions in accordance with the present invention:

Example 1

A. Preparation of Lotion Composition

A water free lotion composition (Lotion A) is made by mixing the following melted (i.e., liquid) components together: Mineral Oil (Carnation White Mineral Oil, USP made by Witco Corp.); Cetearyl Alcohol (a mixed linear $C_{16}$–$C_{18}$ primary alcohol made by the Procter & Gamble Company under the name TA-1618); and Steareth-2 (Brij 72, a $C_{18}$ linear alcohol ethoxylate having an average degree of ethoxylation of 2, made by ICI America). The weight percentages of these components are shown in Table I below:

TABLE I

| Component | Weight % |
|---|---|
| Mineral Oil | 50 |
| Cetearyl Alcohol | 35 |
| Steareth-2 | 15 |

B. Preparation of Lotioned Diaper Leg Cuff by Hot Melt Coating

Lotion Composition A is placed into a heated tank operating at a temperature of 170° F. The composition is subsequently applied with a contact applicator (i.e., a Meltex EP45 hot melt adhesive applicator head operating at a temperature of 170° F.) onto the outer surface of the barrier leg cuffs of a diaper in a 1.4 inch wide (diaper lateral direction) and 11.75 inch long (diaper longitudinal direction) area, the patch centered in the contracted area of the leg cuff. Add-on level =0.0116 g/in$^2$ (18.0 g/m$^2$).

Example 2

The lotion composition A (prepared in accordance with the procedure in Example 1) is subsequently applied onto the outer surface of the barrier leg cuffs of a diaper in a 1.4 inch wide (diaper lateral direction) stripe centered on the longitudinal centerline of each leg cuff and extending the entire length of the leg cuff. Add-on level=0.0116 g/in$^2$ (18 g/m$^2$).

Example 3

The lotion composition A (prepared in accordance with the procedure in Example 1) is subsequently applied onto the outer surface of the barrier leg cuffs of a diaper in a 1.4 inch wide (diaper lateral direction) stripe centered on the longitudinal centerline of each leg cuff and 11.75 inch long (diaper longitudinal direction) area, the patch centered in the contracted area of the leg cuff. Add-on level=0.0077 g/in$^2$ (12.0 g/m$^2$).

Example 4

A. Preparation of Lotion Composition

A water free lotion composition (Lotion B) is made by mixing the following melted (i.e., liquid) components together: Mineral Oil (Carnation White Mineral Oil, USP made by Witco Corp.); and Cetearyl Alcohol (a mixed linear $C_{16}$–$C_{18}$ primary alcohol made by the Procter & Gamble Company under the name TA-1618). The weight percentages of these components are shown in Table II below:

TABLE II

| Component | Weight % |
|---|---|
| Mineral Oil | 65 |
| Cetearyl Alcohol | 35 |

B. Preparation of Lotioned Leg Cuffs by Hot Melt Coating

Lotion Composition B is placed into a heated tank operating at a temperature of 170° F. The composition is subsequently applied with a contact applicator (i.e., a Meltex EP45 hot melt adhesive applicator head operating at a temperature of 170° F.) onto the barrier leg cuffs of a diaper in a 1.4 inch wide (diaper lateral direction) and 11.75 inch long (diaper longitudinal direction) area, the patch centered in the contracted area of the leg cuff. Add-on level=0.0116 g/in$^2$ (18.0 g/m$^2$).

Example 5

A. Preparation of Lotion Composition

A water free lotion composition (Lotion C) is made by mixing the following melted (i.e., liquid) components together: White Protopet® 1S (white petrolatum made by Witco Corp.); Stearyl Alcohol (a linear $C_{18}$ primary alcohol made by the Procter & Gamble Company under the name CO-1897B); and Veragel 1:1 Lipoid with Kaydol (aloe extract made by Dr. Madis Laboratories, Inc.). The weight percentages of these components are shown in Table III below:

TABLE III

| Component | Weight % |
|---|---|
| WhiteProtopet ® 1S | 58 |
| Stearyl Alcohol | 41 |
| Aloe | 1 |

Preparation of Lotioned Diaper by Hot Melt Coating

Lotion Composition C is placed into a heated tank operating at a temperature of 170° F. The composition is subsequently applied with a contact applicator (i.e., a Meltex EP45 hot melt adhesive applicator head operating at a temperature of 170° F.) onto the barrier leg cuffs of a diaper in a 1.4 inch wide (diaper lateral direction) and 11.75 inch long (diaper longitudinal direction) area, the patch centered in the contracted area of the leg cuff. Add-on level=0.0116 g/in$^2$ (18.0 g/m$^2$).

Example 6

A. Preparation of Lotion Composition

A water free lotion composition (Lotion D) is made by mixing the following melted (i.e., liquid) components together: White Protopete 1S (white petrolatum made by Witco Corp.); Cetearyl Alcohol (a mixed linear $C_{16}$–$C_{18}$ primary alcohol made by the Procter & Gamble Company under the name TA-1618); Ceteareth 10 a $C_{16}$–$C_{18}$ linear alcohol ethoxylate having an average degree of ethoxylation of 10, made by ICI America; and Veragel 1:1 Lipoid with Kaydol (aloe extract in mineral oil made by Dr. Madis Laboratories, Inc.). The weight percentages of these components are shown in Table IV below:

TABLE IV

| Component | Weight % |
|---|---|
| WhiteProtopet ® 1S | 49 |
| Stearyl Alcohol | 35 |
| Ceteareth 10 | 15 |
| Aloe | 1 |

B. Preparation of Lotioned Diaper by Hot Melt Coating

Lotion Composition D is placed into a heated tank operating at a temperature of 170° F. The composition is subsequently applied with a contact applicator (i.e., a Meltex EP45 hot melt adhesive applicator head operating at a temperature of 170° F.) onto the barrier leg cuffs of a diaper in a 1.4 inch wide (diaper lateral direction) and 11.75 inch long (diaper longitudinal direction) area, the patch centered in the contracted area of the leg cuff. Add-on level=0.0116 g/in$^2$ (18.0 g/m$^2$).

What is claimed is:

1. An absorbent article having two longitudinal side edges, said absorbent article D comprising:
   A) a backsheet;
   B) a topsheet;
   C) an absorbent core positioned between said topsheet and said backsheet; and
   D) a barrier leg cuff disposed adjacent each of two said longitudinal side edges, wherein each of said barrier leg cuffs has a proximal edge affixed adjacent to said longitudinal side edge of said absorbent article and a distal edge unsecured to at least a portion of said absorbent article, wherein each of said barrier leg cuffs has an inner surface oriented toward the interior of said absorbent article and an outer surface oriented toward the skin of the wearer when said absorbent article is being worn, wherein at least a portion of said barrier leg cuff outer surface or inner surface has disposed thereon an effective amount of a lotion coating which is semi-solid or solid at 20° C. and which is at least partially transferable to the wearer's skin, said lotion coating comprising:
   (i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, and mixtures thereof; and
   (ii) from about 5 to about 90% of an agent capable of immobilizing said emollient on said outer surface or said inner surface of the barrier leg cuff, said immobilizing agent having a melting point of at least about 35° C., said immobilizing agent is selected form the grou consisting of waxes C14–C22 fatty alcohols, C12–C22 fatty acids C12–C22 fatty alcohol ethoxylates nolyhvdroxy fatty acid amides polyhydroxy fatty acid esters having the formula:

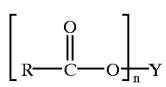

wherein R is a C5–C31 hydrocarbyl group; Y is a polyhydroxyhydrocarbyl moiety having a hydrocarbvl chain with at least 2 free hvdroxuls directly connected to the chain and is selected from the group consisting of polyols, sugars, sugar alcohols, and mixtures thereof, and n is at least one.

2. The absorbent article of claim 1 wherein said lotion coating further comprises from about 0.1% to about 20% of aloe extract.

3. The absorbent article of claim 2 wherein said emollient contains about 5% or less water and comprises a petroleum based emollient selected from the group consisting of mineral oil, petrolatum, and mixtures thereof.

4. The absorbent article of claim 3 wherein said emollient is petrolatum.

5. The absorbent article of claim 3 wherein said emollient is mineral oil.

6. The absorbent article of claim 1 wherein the quantity of lotion coating on said portion of said barrier leg cuff outer surface or inner surface ranges from about 0.1 mg/in$^2$ to about 50 mg/in$^2$.

7. The absorbent article of claim 6 wherein the quantity of lotion coating on said portion of said barrier leg cuff outer surface or inner surface ranges from about 1 mg/in$^2$ to about 25 mg/in$^2$.

8. The absorbent article of claim 1 wherein said lotion coating comprises from about 5 to about 50% of said immobilizing agent, said immobilizing agent having a melting point of at least about 40° C.

9. The absorbent article of claim 8 wherein said immobilizing agent comprises a $C_{14}$–$C_{22}$ fatty alcohol.

10. The absorbent article of claim 9 wherein said immobilizing agent comprises a $C_{16}$–$C_{18}$ fatty alcohol selected from the group consisting of cetyl alcohol, stearyl alcohol, and mixtures thereof.

11. The absorbent article of claim 2 wherein said immobilizing agent comprises a polyhydroxy fatty acid ester selected from the group consisting of sorbitan palmitates, sorbitan stearates, sorbitan behenates, glyceryl monostearate, glyceryl monopalmitate, glyceryl monobehenate, sucrose mono- and di- stearate, and sucrose mono- and di- laurate.

12. The absorbent article of claim 11 wherein said immobilizing agent comprises sorbitan stearates.

13. The absorbent article of claim 2 wherein said immobilizing agent comprises a polyhydroxy fatty acid amide selected from the group consisting of N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, and N-tallowyl-N-methoxypropyl glucamide.

14. The absorbent article of claim 1 wherein said immobilizing agent comprises a paraffin wax.

15. The absorbent article of claim 1 wherein said lotion coating further comprises from about 1 to about 50% of a hydrophilic surfactant, said hydrophilic surfactant having an HLB value of at least about 4.

16. The absorbent article of claim 15 wherein said hydrophilic surfactant comprises an ethoxylated alcohol having an alkyl chain of from about 8 to about 22 carbon atoms and having an average degree of ethoxylation ranging from about 1 to about 54.

17. The absorbent article of claim 16 wherein said ethoxylated alcohol has an alkyl chain of from about 11 to about 22 carbon atoms and having an average degree of ethoxylation ranging from about 2 to about 30.

18. The absorbent article of claim 17 wherein said hydrophilic surfactant comprises an ethoxylated sorbitan ester of a $C_{12}$–$C_{18}$ fatty acid having an average degree of ethoxylation of from about 2 to about 20.

19. The absorbent article of claim 6 wherein said emollient is petrolatum and wherein said immobilizing agent comprises a $C_{16}$–$C_{18}$ fatty alcohol selected from the group consisting of cetyl alcohol, stearyl alcohol, and mixtures thereof.

20. The absorbent article of claim 1 wherein said absorbent article has an elastically contractible gasketing cuff disposed adjacent each of said two longitudinal side edges of said absorbent article, said gasketing cuffs extending laterally outward from said absorbent article longitudinal side edges, wherein each of said gasketing cuffs has a front surface oriented toward the skin of the wearer when said absorbent article is being worn and a back surface opposed to said front surface, wherein at least a portion of said gasketing cuff front surface or back surface has disposed thereon an effective of a lotion coating which is semi-solid or solid at 20° C. and which is at least partially transferable to the wearer's skin, said lotion coating comprising:

(i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, and mixtures thereof, and (ii) from about 5 to about 90% of an agent capable of immobilizing said emollient on said front surface or back surface of said gasketing leg cuff, said immobilizing agent having a melting point of at least about 35° C., said immobilizing agent is selected form the group consisting of waxes C14–C22 fatty alcohols C12–C22 fatty acids C12–C22 fatty alcohol ethoxylates, polyhydroxy fatty acid amides polyhydroxy fatty acid esters having the formula:

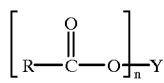

wherein R is a C5–C31 hydrocarbyl group; Y is a polyhydroxyhydrocarbyl moiety having a hydrocarbyl chain with at least 2 free hydroxyls directly connected to the chain and is selected from the group consisting of polyols, sugars, sugar alcohols, and mixtures thereof, and n is at least one.

21. The absorbent article of claim 20 wherein said lotion coating further comprises from about 0.1% to about 20% of aloe extract.

22. The absorbent article of claim 21 wherein said emollient contains about 5% or less water and comprises a petroleum based emollient selected from the group consisting of mineral oil, petrolatum, and mixtures thereof.

23. The absorbent article of claim 22 wherein said emollient is petrolatum.

24. The absorbent article of claim 22 wherein said emollient is mineral oil.

25. The absorbent article of claim 20 wherein the quantity of lotion coating on said portion of said gasketing cuff front surface or back surface ranges from about 0.1 mg/in$^2$ to about 50 mg/in$^2$.

26. An absorbent article having two longitudinal side edges, said absorbent article comprising:
A) a backsheet;
B) a topsheet;
C) an absorbent core positioned between said topsheet and said backsheet; and
D) an elastically contractible gasketing cuff disposed adjacent each of two said longitudinal side edges, said gasketing cuffs extending laterally outward from said absorbent article longitudinal side edges, wherein each of said gasketing leg cuffs has a front surface oriented toward the skin of the wearer and a back surface opposed to said front surface, wherein at least a portion of said gasketing leg cuff front surface or back surface has disposed thereon an effective amount of a lotion coating which is semi-solid or solid at 20° C. and which is at least partially transferable to the wearer's skin, said lotion coating comprising:

(i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, and mixtures thereof; and (ii) from about 5 to about 90% of an agent capable of immobilizing said emollient on said front surface or back surface of the gasketing leg cuff, said immobilizing agent having a melting point of at least about 35° C., said immobilizing agent is selected form the group consisting of waxes, C14–C22 fatty alcohols, C12–C22 fatty acids, C12–C22 fatty alcohol ethoxylates, polyhydroxy fatty acid amides, polyhydroxy fatty acid esters having the formula:

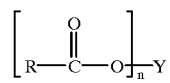

wherein R is a C5–C31 hydrocarbyl group; Y is a polyhydroxyhydrocarbyl moiety having a hydrocarbyl chain with at least 2 free hydroxyls directly connected to the chain and is selected from the group consisting of polyols, sugars, sugar alcohols, and mixtures thereof, and n is at least one.

27. The absorbent article of claim 26 wherein said lotion coating further comprises from about 0.1% to about 20% of aloe extract.

28. The absorbent article of claim 27 wherein said emollient contains about 5% or less water and comprises a petroleum based emollient selected from the group consisting of mineral oil, petrolatum, and mixtures thereof.

29. The absorbent article of claim 28 wherein said emollient is petrolatum.

30. The absorbent article of claim 28 wherein said emollient is mineral oil.

31. The absorbent article of claim 26 wherein the quantity of lotion coating on said portion of said gasketing cuff front surface or back surface ranges from about 0.1 mg/in$^2$ to about 50 mg/in$^2$.

32. The absorbent article of claim 31 wherein the quantity of lotion coating on said portion of said gasketing cuff front surface or back surface ranges from about 1 mg/in$^2$ to about 25 mg/in$^2$.

33. The absorbent article of claim 19 wherein said lotion coating further comprises from about 0.1% to about 20% of aloe extract.

* * * * *

UNITED STATES PATENT AND TRADEMARK OFFICE
CERTIFICATE OF CORRECTION

PATENT NO. : 6,156,024
DATED : December 5, 2000
INVENTOR(S) : Schulte et al.

It is certified that error appears in the above-identified patent and that said Letters Patent is hereby corrected as shown below:

Column 2,
Line 2, delete "wearers" and insert therefor -- wearer's --.

Column 8,
Line 4, delete "wearers" and insert therefor -- wearer's --.

Column 9,
Line 67, delete "Nos." and insert therefor -- No. --.

Column 14,
Line 36, delete "B14,662,875" and insert therefor -- B1 4,662,875 -- (with a space between the "B1" and the "4").

Column 15,
Line 34, delete "071637,090" and insert therefor-- 07/637,090 --.

Column 22,
Line 64, delete "S. P." and insert therefor -- S.P. -- (no space between first period and the "P").

Column 23,
Line 41, delete "IGOOMS" and insert therefor -- 1000MS --.

Column 25,
Line 17, delete "cuffs" and insert therefor -- cuff's --.
Line 22, delete "loton" and insert therefor -- lotion --.
Line 36, delete "wearers" and insert therefor -- wearer's --.
Line 45, after "cuff" insert therefore -- ")" -- (right parenthesis).

Column 28,
Line 42, delete "Protopete" and insert therefor -- Protopet® --.

Column 29,
Line 6, after "article" delete "D".
Line 36, delete "form" and insert therefor -- from --.
Line 37, delete "grou" and insert therefor -- group --.
Line 38, after "acids" insert -- , -- (a comma).
Line 39, after "amides" insert -- , -- (a comma).
Lines 48-49, delete "hydrocarbvl" and insert therefor -- hydrocarbyl --.
Line 49, delete "hvdroxuls" and insert therefor -- hydroxyls --.
Line 56, delete "claim 2" and insert therefor -- claim 1 --.

UNITED STATES PATENT AND TRADEMARK OFFICE
CERTIFICATE OF CORRECTION

PATENT NO.   : 6,156,024
DATED        : December 5, 2000
INVENTOR(S)  : Schulte et al.

It is certified that error appears in the above-identified patent and that said Letters Patent is hereby corrected as shown below:

<u>Column 30,</u>
Line 14, delete "claim 2" and insert therefor -- claim 1 --.
Line 23, delete "claim 2" and insert therefor -- claim 1 --.
Line 65, between "effective" and "of" insert therefor -- amount --.

<u>Column 31,</u>
Line 6, after "thereof" delete "," (the comma).
Line 11, delete "form" and insert therefor -- from --.
Line 12, after "waxes" insert "," (a comma).
Line 13, after "acids" insert "," (a comma).
Line 14, after "amides" insert "," ( a comma).
Line 22, delete "hvdrocarbyl" and insert therefor -- hydrocarbyl --.
Line 24, delete "hvdroxvls" and insert therefor -- hydroxyls --.
Line 30, delete "claim 21" and insert therefor -- claim 20 --.

<u>Column 32,</u>
Line 15, delete "form" and insert therefor -- from --.
Line 26, delete "hydrocarbvl" and insert therefor -- hydrocarbyl --.
Line 35, delete "claim 27" and insert therefor -- claim 26 --.

Signed and Sealed this

Twelfth Day of November, 2002

*Attest:*

JAMES E. ROGAN
*Attesting Officer*    *Director of the United States Patent and Trademark Office*